United States Patent [19]

Wehling et al.

[11] Patent Number: 5,223,264
[45] Date of Patent: Jun. 29, 1993

[54] PEDIATRIC EFFERVESCENT DOSAGE FORM

[75] Inventors: Fred Wehling, New Hope; Steve Schuehle, Minneapolis; Navayanarao Madamala, Plymouth, all of Minn.

[73] Assignee: Cima Labs, Inc., Minneapolis, Minn.

[21] Appl. No.: 750,883

[22] Filed: Aug. 26, 1991

Related U.S. Application Data

[63] Continuation of Ser. No. 416,152, Oct. 2, 1989, abandoned.

[51] Int. Cl.⁵ .................. A61K 9/46; A61K 33/42; A61K 33/34; A61K 33/32; A61K 33/26; A61K 33/24; A61K 33/04; A61K 31/70; A61K 31/56; A61K 31/525; A61K 31/51; A61K 31/44; A61K 31/355; A61K 31/34; A61K 31/12; A61K 31/07; A61L 9/04

[52] U.S. Cl. ........................ 424/466; 424/44; 424/601; 424/630; 424/643; 424/646; 424/655; 424/702; 514/52; 514/169; 514/251; 514/276; 514/356; 514/458; 514/474; 514/681; 514/725; 514/904; 514/905

[58] Field of Search ............... 424/44, 466, 601, 630, 424/643, 646, 702, 655; 514/169, 725, 458, 681, 474, 276, 251, 356, 52, 904, 905

[56] References Cited

U.S. PATENT DOCUMENTS

| | | | |
|---|---|---|---|
| 117,942 | 8/1871 | Taylor | 424/44 |
| 471,879 | 3/1892 | Myers | 424/44 |
| 1,262,888 | 4/1918 | Westlake | 424/44 |
| 1,983,954 | 12/1934 | Taylor | 424/44 |
| 2,092,742 | 3/1937 | Pauley | 424/44 |
| 2,211,485 | 9/1933 | Zimmermann | 424/44 |
| 2,887,437 | 5/1959 | Klioze et al. | 424/44 |
| 3,024,165 | 3/1962 | Murphy | 424/44 |
| 3,495,001 | 2/1970 | Leonards | 424/44 |
| 3,629,468 | 12/1971 | Andersen | 424/44 |
| 3,772,431 | 11/1973 | Milkvy et al. | 424/44 |
| 3,882,228 | 5/1975 | Boncey et al. | 424/44 |
| 3,886,265 | 5/1975 | Evers et al. | 514/159 |
| 3,903,255 | 9/1975 | Gusman et al. | 424/44 |
| 3,947,566 | 3/1976 | Sarna et al. | 424/45 |
| 4,265,874 | 5/1981 | Bonsen et al. | 424/44 |
| 4,414,198 | 11/1983 | Michaelson | 424/44 |
| 4,487,757 | 12/1984 | Kiozpeoplou | 424/7.1 |
| 4,613,497 | 9/1986 | Chavkin | 424/44 |
| 4,639,368 | 1/1987 | Niazi et al. | 424/44 |
| 4,687,662 | 8/1987 | Schobel | 424/44 |
| 4,725,427 | 2/1988 | Ashmead et al. | 514/474 |
| 4,753,792 | 6/1988 | Aberg | 424/44 |
| 4,818,518 | 4/1989 | Gioffre et al. | 424/44 |
| 4,942,039 | 7/1990 | Duvall et al. | 424/466 |
| 5,055,306 | 10/1991 | Barry et al. | 424/482 |

FOREIGN PATENT DOCUMENTS

| | | |
|---|---|---|
| 0219337 | 4/1987 | European Pat. Off. |
| 0313328 | 4/1989 | European Pat. Off. |
| 0396335 | 11/1990 | European Pat. Off. |
| 2190408 | 12/1974 | France |
| 0003160 | of 1872 | United Kingdom ............ 424/466 |

OTHER PUBLICATIONS

S. I. Saleh, "An Approach to the Direct Compression of Effervescent Tablets" Lab Pharmacotech, Fac. Pharmf-67048, Strasbourg Cedex., (1983).

*Primary Examiner*—Frederick E. Waddell
*Assistant Examiner*—Raymond J. Henley, III
*Attorney, Agent, or Firm*—Lerner, David, Littenberg, Krumholz & Mentlik

[57] ABSTRACT

The present invention relates to oral effervescent dosage forms for the administrations of an intended ingredient to children, and processes for their administration.

9 Claims, No Drawings

PEDIATRIC EFFERVESCENT DOSAGE FORM

This is a continuation of application Ser. No. 07/416,152, filed Oct. 2, 1989, now abandoned.

TECHNICAL FIELD

The present invention relates to the field of oral effervescent dosage forms for the administration of an intended ingredient to children.

BACKGROUND OF THE INVENTION

Children generally do not like to take medicine, vitamins, minerals or dietary supplements. Most children dislike medicine because of its flavor. This problem becomes particularly acute when the medicine, vitamin, mineral or dietary supplement must be taken on a daily basis.

In an attempt to make medicine, vitamins, minerals, dietary supplements, and the like, more palatable to children, a number of techniques have been employed. Many pediatric medicines are formulated with large amounts of sweeteners and flavorants to mask the taste of the active ingredients. For example, common children's multivitamin pills include sweeteners and flavorants together with vitamins and minerals. U.S. Pat. No. 2,887,437 relates to a palatable vitamin tablet containing an amino acid. The tablet is designed to be swallowed whole, chewed without objectionable taste, dissolved in the mouth, or dissolved in liquids. It contains a plurality of vitamins, a nutritionally essential amino acid, a flavoring agent, and a hydrophilic starch as a disintegration agent. Flavored disintegrable pills have, however, been generally ineffective in overcoming children's reluctance to taking medicines and particularly vitamins which generally require daily administration. While these pills are less objectionable than other dosage forms, the flavor is often overpowered by the taste of the medicine.

Another approach to the administration of medicines, vitamins, minerals, and the like to person s in general is the use of effervescent tablets. Effervescence can be defined as the evolution of bubbles of gas in a liquid. As set forth in chapter 6 of *Pharmaceutical Dosage Forms: Tablets Volume I*, 2nd Edition, A. Lieberman, ed. 1989, Marcel Dekker, Inc. (the entirety of which is hereby incorporated by reference), effervescent mixtures have been known and used medicinally for many years. As discussed in this text, and as commonly employed in the medical and pharmaceutical communities, an effervescent tablet is dissolved in water to provide a carbonated or sparking liquid drink. In such a drink the effervescence helps to mask the taste of medicaments. As briefly mentioned in Saleh, *An Approach to the Direct Compression of Effervescence Tablets: Chemical Properties of the Ingredients*, Lab. Pharmacotech, Fac. Pharmf-67048 Strasborg Cedex. from the Department of Industrial Pharmacy, Faculty of Pharmacy, Assiout (Egypt), and for the reasons discussed above, effervescent tablets occupy an important position as dosage forms not only for adults, but also for children. However, the use of effervescent tablets to prepare a beverage including medicaments, is not always convenient.

In a departure from the traditional use of effervescence, U.S. Pat. No. 4,639,368 described a chewing gum containing a medicament and a taste-masker. The taste-masker is a generator of carbon dioxide and in an optional embodiment a taste bud desensitizing compound. This type of direct oral dosage form has certain advantages, however, the disadvantages inherent in a gum based delivery system present problems. Gums are difficult to prepare. Because of braces or other dental work, many children are not permitted to chew gum. Furthermore, if the flavor and/pr the effervescent "taste masker" react and/or fade prior to the full release of medicament, the child will be left with a gum having an objectionable taste. Finally, gums leave residues which must be properly disposed of.

Thus there remains a need for a convenient and effective dosage form for intended ingredients which may be consumed by all children, including those who can't chew a gum or swallow a pill and will be readily accepted thereby.

SUMMARY OF THE INVENTION

One aspect of the present invention provides an oral pediatric vitamin supplement comprising a mixture of at least one effervescent disintegration agent, and a pediatrically effective amount of at least one intended ingredient selected from the group consisting of vitamins and minerals and mixtures thereof. The mixture most preferably is present in the form a compressed tablet of a size and shape adapted for direct oral administration to children and which will rapidly and completely disintegrate when administered. The effervescent disintegration agent is present in an amount which is effective both to aid in the rapid disintegration of the tablet and to provide a positive organoleptic sensation to children.

Another aspect of the present invention provides an oral pediatric dosage form comprising a mixture of at least one effervescent disintegration agent, and a pediatrically effective amount of at least one intended ingredient, wherein said mixture is present in the form of a compressed tablet of a size and shape adapted for direct oral administration to children and which will rapidly and completely disintegrate when administered; and wherein said effervescent disintegration agent is present in an amount which is effective both to aid in the rapid disintegration of said tablet and to provide a positive organoleptic sensation to children. According to this aspect of the present invention, the intended ingredient may include, without limitation, pharmaceuticals, minerals, vitamins and dietary supplements and mixtures thereof.

These aspects of the present invention incorporate the discovery that provision of an effervescent effect in an oral disintegrable tablet is a factor which results in materially enhanced acceptance of the tablet by children.

Children readily accept the tablets of the present invention, not only because the effervescent disintegration agent provides for the controlled and rapid disintegration of the tablet when placed in the mouth or because the effervescent disintegration agent, by its action, aids in the masking of the potentially objectionable tastes of the vitamins, medicines and/or minerals. Rather, it is the positive organoleptic sensation achieved by the effervescent action in the mouth, the texture, speed and sensation of disintegration, and the size and shape of the tablet which is adapted for children which, in combination, result in breaking down children's apprehension to taking the tablet. The combined sensations achieved by the preferred dosage forms according to this aspect of the present invention are accepted by children to a surprising degree. It has been found that children enjoy both the taste and the tactile sensation of sucking on or chewing an effervescent delivery system of the type described and claimed herein. This is particularly important when, as in the case of vitamins, a child must take a particular intended ingredient on a daily basis. Furthermore, because the positive organoleptic sensation may be realized by either chewing or by sucking on a tablet according to the present invention, the widest range of children may benefit.

In preferred embodiments of the present invention, the effervescent disintegration agent may include, without limitation, at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

In addition to masking the objectionable flavor of medicants, the effervescence of the tablets of the present invention facilitate the disintegration thereof. Furthermore, the use of the effervescent disintegration agent of the present invention provides a pleasant oral organoleptic sensation. Organoleptic is understood to mean being, affecting, or relating to the qualities of the tablets of the present invention, that stimulate the sensory organs. These may include taste, odor, and/or feel of the tablets of the present invention while in the mouth of the child to whom administered.

Another aspect of the present invention provides a process of administering an intended ingredient to a child comprising the steps of: providing a tablet including at least one effervescent disintegration agent, and a pediatrically effective amount of at least one intended ingredient; directly administering said tablet to a child so that said tablet disintegrates in the child's mouth, and promoting disintegration of said tablet and providing a positive organoleptic sensation in the mouth by operation of said effervescent disintegration agent.

DETAILED DESCRIPTION OF THE PREFERRED EMBODIMENT

An oral dosage form according to one embodiment of the present invention is a tablet of a size and shape adapted for direct oral administration to children. The tablet is small enough to be administered to a child. As used in this disclosure, the term "child" refers to a person under the age of about 16 years. The pediatric dosage forms according to this aspect of the invention are preferably useful for children under the age of about 12 years. For children under the age of 12 years, tablets having a volume less than about 2.0 cm$^3$, and desirably less than about 1.0 cm$^3$ are preferred. The mass of each such tablet generally should be less than about 3.0 g and more preferably less than about 1.5 g. The tablet may have the shape of letters, numbers, animals, birds, cartoon characters, fish, dinosaurs, and the like. Further, the tablet may include surface markings, cuttings, grooves, letters and or numerals for the purpose of decoration and/or identification. The tablet is, of course, in solid form. Preferably, the tablet is a hard compressed tablet. It includes one or more intended ingredients, together with an effervescent disintegrating agent.

The term "intended ingredient(s)" is understood to mean an ingredient or ingredients, the ingestion of which is the reason for consuming a tablet in which that ingredient is included. For the purposes of the present invention, an intended ingredient may include pharmaceuticals or pharmaceutically active ingredients, minerals, vitamins and dietary supplements. Mixtures of any of the foregoing are also contemplated by the term intended ingredient.

By the term pharmaceutical or pharmaceutically active ingredient applicants mean a drug. Pharmaceutically active ingredients may include, without limitation, antacids, analgesics, antiinflammatories, antibiotics, laxatives, anorexics, antiasthmatics, antidiuretics, antiflatuents, antimigraine agents, antispasmodics, sedatives, antihyperactives, tranquilizers, antihistamines, decongestants, betablockers, antialcoholism agents, cough suppressants, fluoride supplements, antiseptics and combinations thereof.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyrodoxine, biotin, folic acid, vitamin $B_{12}$, lipoic acid, ascorbic acid, vitamin A, vitamin D, vitamin E and vitamin K. Also included with the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP) Coenzyme A (CoA) pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administrated in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

The amount of intended ingredient incorporated in each tablet may be selected according to known principles of pharmacy. An effective amount of intended ingredient is specifically contemplated. By the term effective amount, it is understood that, with respect to for example pharmaceuticals, a pharmaceutically effective amount is contemplated. A pharmaceutically effective amount is the amount or quantity of a drug or pharmaceutically active substance which is sufficient to elicit the required or desired therapeutic response. A pediatrically effective amount, as used herein, refers to the amount of a vitamin, pharmaceutical, mineral and/or dietary supplement which is sufficient to elicit an appreciable biological response when administered to a child. As used with reference to a vitamin or mineral, the term "pediatrically effective amount" means an amount at least about 10% of the United States Recommended Daily Allowance ("RDA") of that particular ingredient for children. For example, if an intended ingredient is vitamin C, then a pediatrically effective amount of vitamin C would include an amount of vitamin C sufficient to provide 10% or more of the RDA.

Typically, where the table includes a mineral or vitamin, it will incorporate higher amounts, preferably about 100% or more of the applicable RDA.

The term effervescent disintegration agent(s) includes compounds which evolve gas. The preferred effervescent agents evolve gas by means of chemical reactions which take place upon exposure of the effervescent disintegration agent to saliva in the mouth.

The bubble or gas generating reaction is most often the result of the reaction of a soluble acid source and an alkali metal carbonate or carbonate source. The reaction of these two general classes of compounds produces carbon dioxide gas upon contact with water included in saliva.

Such water activated materials must be kept in a generally anhydrous state with little or not absorbed moisture or in a hydrated form since exposure to water will prematurely disintegrate the tablet. The acid sources or acid may be any which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations of the present invention were intended to the dissolved in a glass of water. Acid anhydrides and acid of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesequicarbonate, sodium glycine carbonate, L-lysine carbonate, arginine carbonate and amorphous calcium carbonate.

The effervescent disintegration agent of the present invention is not always based upon a reaction which forms carbon dioxide. Reactants which evolve oxygen or other gasses which are pediatrically safe are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

In general, the amount of effervescent disintegration agent of the present invention useful for the formation of tablets according to the present invention should range from about 5 to about 50% by weight of the final composition, and preferably between about 15 and about 30% by weight thereof. In a more preferred embodiment, the amount of effervescent disintegration agent according to the present invention ranges from between about 20 and about 25% by weight of the total composition.

More specifically, tablets according to the present invention should contain an amount of effervescent disintegration agent effective to aid in the rapid and complete disintegration of the tablet when orally administered to children. By "rapid", it is understood that the tablets of the present invention should disintegrate in the mouth of a child in less than 10 minutes, and desirably between about 30 seconds and about 7 minutes. In a particularly preferred embodiment according to the present invention, the tablet should dissolve in the mouth of a child in between about 30 seconds and about 5 minutes. Disintegration time in the mouth can be measured by observing the disintegration time of the tablet in water at about 37° C. The tablet is immersed in the water without forcible agitation. The disintegration time is the time from immersion for substantially complete dispersion of the tablet as determined by visual observation. Disintegration times referred to in this disclosure should be understood as determined by this method unless otherwise specified.

Also, the amount of effervescent disintegration agent present in the tablet should be effective to provide an effervescent sensation in the mouth of the child who consumes the tablet. Thus, the child should be able to perceive a distinct sensation of "fizzing" or bubbling as the tablet disintegrates in the mouth. To provide this sensation, the amount of effervescent agent in each tablet desirably is arranged to provide about 20 to about 60 $cm^3$ of gas. The "fizzing" sensation substantially enhances the organoleptic effects of the tablet. Thus, the amount of effervescent disintegration agent useful in accordance with the present invention is also an amount effective to provide a positive organoleptic sensation of children. A "Positive" organoleptic sensation is one which is pleasant or enjoyable and which can be perceived readily.

It should also be noted that the hardness of a tablet may also play a role in disintegration time. Specifically, increasing the hardness of a tablet may increase the disintegration time just as decreasing hardness may decrease disintegration time.

The dosage form according to this aspect of the present invention may further include one or more additional adjuvants which can be chosen from those known in the art including flavors, dilutents, colors, binders, filler, compaction vehicles, and non-effervescent disintegrants.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Non-effervescent disintegrants include starches as corn starch, potato starch and modified starches thereof, sweeteners, clays, such as bentonite, microcrystalline cellulose, alginates, gums such as agar, guar, locust bean, karaya, pecitin and tragacanth. Disintegrants may comprise up to about 20 weight percent and preferably between about 2 and about 10 percent of the total weight of the composition.

Coloring agents may include titanium dioxide, and dyes suitable for food such as those known as F.D.&C. dyes and natural coloring agents such as grape skin extract, beet red powder, beta-carotene, annato, carmine, turmeric, paprika, etc. The amount of coloring used may range from about 0.1 to about 3.5 weight percent of the total composition.

Flavors, incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple pear, peach, strawberry, raspberry, cherry, plum pineapple, apricot and so forth, Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.5 to about 3.0 by weight based upon the weight of the composition. Particularly preferred flavors are the orange, grape and cherry flavors.

Tablets according to this aspect of the present invention can be manufactured by well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minutes can be produced in this fashion. Various tableting methods, well known to those skilled in the art, are comprehensively discussed in Lieberman, *Pharmaceutical Dosage Forms: Tablets Volume* 1, Second Edition, Revised and Expanded Copyright 1989 by Marcel Dekker Inc.

Materials to be delivered are often pretreated either alone or in combination with other fillers to form granules that readily lend themselves to tableting. This process is known as granulation. As commonly defined, "granulation" is any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation. IN granulation, active or intended ingredients are generally admixed with a compression vehicle incorporating the effervescent disintegration agent and other adjuvants referred to above. The compression vehicle or filler should have good compressibility, good flowability and stability under normal ambient conditions as well as being low in cost and satisfactory in both texture and appearance.

As noted in Chapter 6 of *Pharmaceutical Dosage Forms,* supra, lubricants normally are used in manufacture of effervescent tablets. Without the use of an effective lubricant, tableting by use of today's high speed equipment would not be possible. Effervescent granulations are inherently difficult to lubricate due to both the nature of the raw materials and the requirement that the tablets disintegrate rapidly.

Lubricant, as used herein, means a material which can reduce the friction arising at the interface of the tablet and the die wall during compression and ejection thereof. Lubricants may also serve to prevent sticking to the punch and, to a lesser extent, the die wall as well. The term "antiadherents" is sometimes used to refer specifically to substances which function during ejection. As used in the present disclosure, however, the term "lubricant" is used generically and includes "antiadherents". Tablet sticking during formation and/or ejection may pose serious production problems such as reduced efficiency, irregularly formed tablets, and non-uniform distribution of intended agents or ingredients to be delivered thereby. These problems are particularly severe with high speed tableting approaches and methods.

Lubricants may be intrinsic or extrinsic. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity.

Intrinsic lubricants are incorporated in the material to be tableted. Magnesium, calcium and zinc salts of stearic acid have long been regarded as the most efficient intrinsic lubricants in common use. Concentrations of one percent or less are usually effective.

Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, magnesium oxide and the like. See European Patent Application No. 0,275,834, the disclosure of which is incorporated by reference. See also Leal, et al., U.S. Pat. No. 3,042,531.

Lubricants, according to the present invention, may be used in an amount of up to 1.5 weight percent and preferably between about 0.5 and about 1.0 weight percent of the total composition.

Intrinsic lubricants pose certain serious difficulties when used in conventional tablets. Many lubricants materially retard the disintegration of non-effervescent tablets. However, the effervescent disintegration agents used in the dosage form of the present invention overcome any such retardation. IN dissolution of conventional effervescent tablets, the lubricant may cause "scumming" and/or agglomeration. Stearates, for example leave an objectionable "scum" when an effervescent tablet is placed in a glass of water. This "scum" reduces the aesthetic appeal of the solution made from an effervescent dosage form. However, because the tablets of the present invention dissolve in the mouth, the solution is never seen by the user. Therefore, the propensity of a lubricant to "scum" is unimportant. Thus, lubricants which can cause dissolution or scumming problems in other dosage forms can be used in dosage forms according to the present invention without material adverse effect.

The foregoing will be better understood with reference to the following examples which detail a particularly preferred procedure for the manufacture of tablets according to the present invention. All references made to these examples are for the purposes of illustration. They are not to be considered limiting as to the scope and nature of the present invention.

EXAMPLE I

The following ingredients were weighed individually and screened through a 10 mesh sieve. These ingredients, except for the magnesium stearate, were then charged to a twin shell blender where they were mixed for 20 min. The propeller of the blender was set at 24 rpm's, and the mixture was processed with tilt but without vacuum. The magnesium stearate was then added to the blended mixture and mixing continued for an additional 5 min. The composition was then formed into tablets by compression using conventional high speed rotary tableting equipment. Specifically, the tableting equipment is arranged to fill a tubular die with the tableting composition. A pair of closely fitting punches are advanced into the die to thereby compress the composition and form tablets thereby. The tablet is ejected from the punch and die assembly. A 2000 tablet batch was made.

| Ingredient | mg/tablet | 2000 tablets (grams) |
|---|---|---|
| Sorbitol | 500.0 | 1000.0 |
| Ascorbic Acid 95% gran | 137.0 | 274.0 |
| Sodium Bicarbonate #1 | 127.0 | 254.0 |
| Citric Acid | 90.0 | 180.0 |
| Potassium Bicarbonate | 25.0 | 50.0 |
| Orange flavor | 20.0 | 40.0 |
| Aspartame | 15.0 | 30.0 |
| Magnesium Stearate | 10.0 | 20.0 |
| Average tablet weight = 924.0 mg. | | |

A one half inch (12.7 mm) diameter standard punch and die set having punches with concave faces was used to form 12.7 mm diameter disc-like tablets with slightly convex faces. The resulting tablets have a solid, smooth appearance. When a tablet is dissolved in the mouth, it provides a pleasant fizzing or bubbling sensation, together with a mild orange flavor.

EXAMPLE II

The following ingredients were weighed and processed as in Example I, except that a standard 5/8 inch (15.9 mm) diameter concave punch and die set was used.

| Ingredient | (orange) mg/tab & average | (grape) mg/tab & |
|---|---|---|
| Sorbitol | 400.0 | 400.0 |
| Ascorbic Acid 95% gran | 342.0 | 342.0 |
| Sodium Bicarbonate #2 | 127.0 | 127.0 |
| Citric Acid | 100.0 | 100.0 |
| Potassium Bicarbonate | 25.0 | 25.0 |
| Dry E Acetate 50% SD | 69.0 | 69.0 |
| Niacinamide 33⅓% | 69.0 | 69.0 |
| Riboflavin 25% | 7.8 | 7.8 |
| Pyridoxine 33⅓ | 6.9 | 6.9 |
| Thiamine 33⅓% | 5.2 | 5.2 |
| Dry A Acetate Type 500 | 12.0 | 12.0 |
| D-Calcium Pantothenate | 12.5 | 12.5 |
| Folic Acid 10% | 5.0 | 5.0 |
| Biotin 1% | 5.0 | 5.0 |
| Aspartame | 25.0 | 25.0 |
| Vitamin $B_{12}$ 0.1% SD | 7.0 | 7.0 |
| Vitamin D3 100 CWS | 4.8 | 4.8 |
| Orange Flavor | 20.0 | — |
| Bell Grape | — | 25.0 |
| Grape Skin Extract | — | 17.0 |
| Powdered Beet Red | — | 13.0 |
| Magnesium Stearate | 12.0 | 12.0 |
| Total Weight: | 1255.2 mg | 1290.2 mg |

A tablet of about 6 mm (0.234") thickness is produced. These tablets have an excellent appearance and provide a pleasant grape flavor together with a fizzing sensation. Tablets according to this example are administered to children along with conventional pediatric multivitamins in a comparison test. Children are asked to state their preference. Tablets according to the example are favored by about 89% of the children.

EXAMPLE III

The following ingredients were weighed and processed as in Example II.

| Ingredient | mg/tab | 3000 tab seg. |
|---|---|---|
| Sorbitol | 200.0 | 600.0 |
| Ascorbic Acid 95% gran. | 82.0 | 246.0 |
| Sodium Bicarbonate #2 | 127.0 | 381.0 |
| Citric Acid | 130.0 | 390.0 |
| Dicalcium Phosphate | 336.0 | 1008.0 |
| Magnesium Phosphate | 91.2 | 273.6 |
| Potassium Bicarbonate | 25.0 | 75.0 |
| Dry Vit. E Acetate 50% SD | 69.0 | 207.0 |
| Niacinamide 33⅓% | 69.0 | 207.0 |
| Riboflavin 25% | 7.8 | 23.4 |
| Pyidoxine 33⅓% | 6.9 | 20.7 |
| Thiamine 33⅓% | 5.2 | 15.6 |
| D-Cal-Pantothenate | 12.5 | 37.5 |
| Dry A Acetate Type 500 | 12.0 | 36.0 |
| Folic Acid 10% | 5.0 | 15.0 |
| Biotin 1% | 5.0 | 15.0 |
| B12 0.1% SD | 7.0 | 21.0 |
| Ferrous Sulfate | 49.0 | 147.0 |
| Aspartame | 30.0 | 90.0 |
| Magnesium Stearate | 12.0 | 36.0 |
| Zinc Oxide | 18.6 | 55.8 |
| Magnesium Oxide | 7.6 | 7.8 |
| Orange Flavor | 20.0 | 60.0 |
| D3 Type 100 CWS | 4.8 | 14.4 |
| Potassium Iodide | 0.2 | 0.6 |
| Copper Gluconate | 0.7 | 2.1 |
| Tablet Weight = 1328.5 mg | | |

A tablet of 5.6 mm (0.222 inches) thickness was produced.

The principles, preferred embodiments, and modes of operation of the present invention has been described in the foregoing specification period. The invention which is intended to be protected herein, however, is not to be construed as limited to the particular embodiments disclosed, since these are to be regarded as illustrative rather than restrictive. Variations and changes may be made by others without departing from the spirit and scope of the invention.

What is claimed is:

1. An oral pediatric vitamin supplement comprising: a mixture of at least one effervescent disintegration agent, and a pediatrically effective amount of at least one intended ingredient selected from the group consisting of vitamins and minerals and mixtures thereof, wherein said mixture is present in the form of a compressed tablet of a size and shape adapted for direct oral administration to children and which will rapidly and completely disintegrate when administered; and wherein said effervescent disintegration agent is present in a amount which is effective to both aid in rapid disintegration of said tablet and to provide a positive organoleptic sensation to children.

2. The vitamin supplement of claim 1, wherein said effervescent disintegration agent is selected from a mixture of at least one acid selected from the group consisting of citric acid, tartaric acid, malic acid, fumaric acid, adipic acid, succinic acid, acid anhydrides of said acids and acid salts of said acids and mixtures thereof, and at least one carbonate source selected from the group consisting of carbonate salts, bicarbonate salts, sesequicarbonate salts and mixtures thereof.

3. The vitamin supplement of claim 1, wherein said vitamin is selected from the group consisting of: thiamine, riboflavin, nicotinic acid, pontotheniacacid, pyridoxine, biotin, folic acid, Vitamin $B_{12}$, cholines carnitine, alpha, beta and gamma carotenes, lipoic acid, ascorbic acid, Vitamin A, Vitamin D, Vitamin E, Vitamin K, coenzymes containing said vitamins, and mixtures thereof.

4. The vitamin supplement of claim 1, further comprising at least one additional adjuvant selected from the group consisting of binders, lubricants, fillers, colors, flavors, and mixtures thereof.

5. The oral pediatric vitamin supplement of claim 1 wherein said mineral is selected from the group consisting of calcium, zinc, iron, selenium, copper, iodine, magnesium, phosphorous, chromium, and mixtures thereof.

6. A process of administering an intended ingredient to a child comprising the step of: providing a tablet including at least one effervescent disintegration agent, and a pediatrically effective amount of at least one intended ingredient; directly administering said tablet to a child so that said tablet disintegrates in the child's mouth, and promoting disintegration of said tablet and providing a positive organoleptic sensation in the mouth by operation of said effervescent disintegration agent, wherein said intended ingredient is selected from the group consisting of vitamins and minerals and mixtures thereof.

7. The process of claim 6, wherein said vitamin is selected from the group consisting of: thiamine, riboflavin, nicotinic acid, pontothenicacid, pyridoxine, biotin, folic acid, Vitamin $B_{12}$, cholines, carnitine, alpha, beta and gamma carotenes, lipoic acid, ascorbic acid, Vitamin A, Vitamin D, Vitamin E, Vitamin K, coenzymes containing said vitamins, and mixtures thereof.

8. The process of claim 6, wherein said mineral is selected from the group consisting of calcium, zinc, iron, selenium, copper, iodine, magnesium, phosphorous, chromium and mixtures thereof.

9. The process of claim 6, wherein said effervescent disintegration agent is selected from a mixture of at least one acid selected from the group consisting of citric acid, tartaric acid, malic acid, fumaric acid, adipic acid, succinic acid, acid anhydrides of said acids and acid salts of said acids and mixtures thereof, and at least one carbonate source selected from the group consisting of carbonate salts, bicarbonate salts, sesequicarbonate salts and mixtures thereof.

* * * * *

UNITED STATES PATENT AND TRADEMARK OFFICE
CERTIFICATE OF CORRECTION

PATENT NO.   :   5,223,264

DATED        :   June 29, 1993

INVENTOR(S)  :   Wehling et al.

It is certified that error appears in the above-identified patent and that said Letters Patent is hereby corrected as shown below:

```
Column 1, line 41, delete "person s" and insert therefor
                   --persons--.
          line 57, "Strasborg" should read --Strasbourg--.
Column 2, line 6,  delete "pr" and insert therefor --or--.
          line 24, after "form" insert --of--.
Column 4, line 27, delete "(AND)" and insert therefor --(NAD)--.
Column 5, line 16, delete "not" and insert therefor --no--.
          line 26, delete "the" (second occurrence) and insert
                   therefor --be--.
Column 7, line 14, after "plum" insert --,--.
          line 50, "IN" should read --In--.
Column 8, line 44, "IN" should read --In--.
Column 11, lines 1-2, "sesequicarbonate" should read
                   --sesquicarbonate--.
Column 11, line 5, "pontotheniacacid" should read
                   --pontothenicacid--.
Column 12, line 24, "sesequicarbonate" should read
                   --sesquicarbonate--.
```

Signed and Sealed this

Twenty-sixth Day of April, 1994

BRUCE LEHMAN

Attest:

Attesting Officer    Commissioner of Patents and Trademarks